United States Patent
Bodas et al.

(10) Patent No.: US 11,724,973 B2
(45) Date of Patent: Aug. 15, 2023

(54) METHODS AND SYSTEMS FOR PROCESSING PENTANES

(71) Applicant: SABIC Global Technologies B.V., Bergen op Zoom (NL)

(72) Inventors: Vijay Dinkar Bodas, Riyadh (SA); Guillermo Canelon Leal, Riyadh (SA); Mohammed B. Ansari, Riyadh (SA); Sami Al Mutairi, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 17/790,243

(22) PCT Filed: Dec. 17, 2020

(86) PCT No.: PCT/IB2020/062125
§ 371 (c)(1),
(2) Date: Jun. 30, 2022

(87) PCT Pub. No.: WO2021/137083
PCT Pub. Date: Jul. 8, 2021

(65) Prior Publication Data
US 2023/0047672 A1 Feb. 16, 2023

(30) Foreign Application Priority Data
Dec. 30, 2019 (EP) .................................... 19220105

(51) Int. Cl.
*C07C 5/27* (2006.01)

(52) U.S. Cl.
CPC ........ *C07C 5/2724* (2013.01); *C07C 2523/42* (2013.01)

(58) Field of Classification Search
CPC ...... C07C 5/2724; C07C 2523/42; C07C 7/04
See application file for complete search history.

(56) References Cited

U.S. PATENT DOCUMENTS

| | | | |
|---|---|---|---|
| 3,922,216 A | 11/1975 | Wilson et al. | |
| 4,324,936 A | 4/1982 | Mikulicz | |
| 10,113,121 B2 | 10/2018 | Pigourier et al. | |
| 2019/0002370 A1 | 1/2019 | Luebke et al. | |

OTHER PUBLICATIONS

Dean et al. "The Penex Process for Pentane Isomerisation." Platinum Metals Rev., 1959, 3, (1), 9-11.
Extended European Search Report from European Application No. 19220105.1 dated Jul. 10, 2020, 5 pages.
International Search Report and Written Opinion from PCT/IB2020/062125 dated Mar. 5, 2021, 9 pages.
Musumeci et al. "Analysis of alky unit DIB exposes design and operating considerations." Ascent Engineering, Inc. 6 pages. Retrieved Sep. 11, 2019. http://ascentengineering.com/alkyDIB.aspx.

*Primary Examiner* — Thuan D Dang
(74) *Attorney, Agent, or Firm* — Norton Rose Fulbright US LLP

(57) ABSTRACT

A method for processing pentanes obtained from a DIB unit is disclosed. The process can include separating a first stream containing pentanes obtained from a DIB unit, in a separation column to obtain a second stream comprising iso-pentane and a third stream comprising n-pentane and neo-pentane; and subjecting the third stream to a butane isomerization unit producing a fourth stream containing iso-pentane, n-pentane, and neo-pentane.

15 Claims, 5 Drawing Sheets

METHODS AND SYSTEMS FOR PROCESSING PENTANES

CROSS REFERENCE TO RELATED APPLICATIONS

This application is a national phase application under 35 U.S.C. § 371 of International Application No. PCT/IB2020/062125 filed Dec. 17, 2020, which claims priority to European Patent Application No. 19220105.1 filed Dec. 30, 2019. The entire contents of each of the above-referenced disclosures is specifically incorporated by reference herein without disclaimer.

BACKGROUND OF THE INVENTION

A. Field of the Invention

The invention generally concerns systems and processes for processing a pentanes stream. In particular, the invention concerns system and processes for processing a pentanes stream from a de-isobutanizer (DIB) unit.

B. Description of Related Art

There is a continuous growing demand for iso-pentanes. Iso-pentanes can be used as solvents, in geothermal production plants, as blend stocks for gasoline and methyl tertiary butyl ether (MTBE), etc. Iso-pentane has an octane number over 90 and can be use as octane boosters. Substantially pure iso-pentane without a high percentage of n-pentane and neo-pentane is preferred because octane number of iso-pentane is higher than that of n-pentane and neo-pentane. Flaring or burning can be minimized with substantially pure iso-pentane i.e., without high percentage of n-pentane and neo-pentane. Pentanes can be obtained from a DIB unit.

Musumeci et al. ("Analysis of alky unit DIB exposes design and operating considerations") describes maximizing yields from a DIB and discloses design and operating considerations that should be addressed when capacity and efficiency improvements are desired. Musumeci et al. doesn't disclose processing a pentanes stream obtained from a DIB unit to produce additional iso-pentane.

While attempts have been made to optimize the process for production of iso-pentane, these processes tend to suffer from inefficient production of substantially pure iso-pentane and/or increased production costs.

SUMMARY OF THE INVENTION

A discovery has been made that provides a solution to some of the afore mentioned problems. The solution is premised on processing a pentanes stream containing iso-pentane, n-pentane and neo-pentane from a DIB unit, separating iso-pentane from n-pentane and neo-pentane to obtain a sufficiently pure iso-pentane, and producing additional iso-pentane from the separated n-pentane and neo-pentane.

In one aspect of the present invention, a method for processing a pentanes stream is described. In certain aspects, the process can include steps (a) or (b) or both (a) and (b). In step (a) a first stream containing pentanes can be separated in a separation column to obtain a second stream containing iso-pentane and a third stream containing n-pentane and neo-pentane. In step (b) the third stream can be fed to a butane isomerization unit producing a fourth stream containing iso-pentane, n-pentane, and neo-pentane. In some aspects, the first stream can be obtained from a DIB unit. In some aspects, the third stream can be desulfurized prior to subjecting the third stream to the butane isomerization unit. In some aspects, the desulfurization process can include absorption and removing of sulfur containing compounds from the third stream by an adsorbent. In some aspects, the adsorbent can be zeolite 13X and/or activated charcoal. In some particular aspects, the desulfurization process can include passing the third stream over and/or through an adsorbent bed such as a zeolite 13X molecular sieve bed or an activated charcoal bed. A spent adsorbent can be formed by absorption of the sulfur containing compounds by the adsorbent. In some aspects, the adsorbent can be regenerated from the spent adsorbent. In the butane isomerization unit the third stream can be contacted with a isomerization catalyst. In some aspects, the third stream can be contacted with the isomerization catalyst under conditions including i) a temperature of 130° C. to 300° C.; ii) a pressure of 10 to 40 bar; iii) a WHSV of 0.5 $h^{-1}$ to 10 $h^{-1}$ or 4 $h^{-1}$ to 6 $h^{-1}$; or any combination thereof.

The isomerization catalyst can be a butane isomerization catalyst known in the art. In some aspects, the isomerization catalyst can be platinum chlorinated alumina ($Pt/Al_2O_3$—Cl) catalyst, platinum zirconia sulfate catalyst ($Pt/ZrO_2$—$SO_4$) and/or a zeolite such as iso shape selective zeolites. In the butane isomerization unit at least a portion of the n-pentane and/or neo-pentane from the third stream can be isomerized to form iso-pentane. In some aspects, a feed stream containing n-butane can be fed to the butane isomerization unit and the fourth stream can further include iso-butane. In some aspects, the feed stream can further contain iso-butane, iso-pentane, n-pentane, and neo-pentane. In some aspects, the feed stream can be desulfurized prior to feeding the feed stream to the butane isomerization unit. In some aspects, the third stream and the feed stream can be fed to the butane isomerization unit as separate feeds. In some other aspects, the third stream and the feed stream can be fed to the butane isomerization unit as a combined feed. In some aspects, the third stream and feed stream can be combined to form the combined feed, the combined feed can be desulfurized and then fed to the butane isomerization unit. In some aspects, the third stream and the feed stream can be combined after desulfurization of the respective streams and the combined feed can be fed to the butane isomerization unit. The fourth stream can be fed to a DIB unit. In some aspects, the fourth stream can be fed to the DIB unit from which the first stream is obtained. In some aspects, the fourth stream can be fed to a DIB unit (second DIB unit), that is different from the DIB unit (first DIB unit) from which the first stream is obtained. In some aspects, the DIB unit can include a DIB column. In some aspects, the DIB column operation condition to obtain the first stream can include a temperature of 30° C. to 80° C., or 40° C. to 70° C., or 50° C. to 60° C. In some aspects, the DIB column operation condition to obtain the first stream can include a reboiler range of 70° C. to 120° C., or 80° C. to 110° C., or 90° C. to 100° C. In some aspects, the DIB column operation condition to obtain the first stream can include an operation gauge pressure of 0.1 bar to 10 bar or 0.2 bar to 8 bar or 0.5 bar to 6 bar or 1 bar to 5 bar. In some aspects, the DIB column operation condition to obtain the first stream can include a temperature of 50° C. to 60° C., a reboiler range of 90 to 100° C., an operation gauge pressure of 1 to 5 bar, or any combination thereof. In some aspects, the DIB column can include 20 to 75, or 30 to 65, or 40 to 55, trays. The first stream can be obtained as a bottom stream from the DIB column. The first stream can contain 30 wt. % to 70 wt. % or 40 wt. % to 60 wt. % iso-pentane. The first stream can contain 10 wt. % to 40 wt. % or 15 wt. % to 35 wt. % n-pentane. The first stream can contain 1 wt. % to 15 wt. % or 2 wt. % to 10 wt. % neo-pentane. In some aspects, the first stream can contain 30 wt. % to 70 wt. % iso-pentane, 15 wt. % to 35 wt. % n-pentane, and 1 wt. % to 15 wt. % neo-pentane. The separation column in step (a) can be a deisopentanizer column. In some aspects, the deisopentanizer column operation condition during the separation of the first stream can include an overhead boiling range temperature of 30° C. to 85° C., or 40° C. to 75° C., or 50° C. to 65° C. In some aspects, the deisopentanizer column operation condition during the separation of the first stream can include a reboiler range of 50° C. to 130° C., or 60° C. to 120° C., or 70° C. to 120° C., or 70° C. to 110° C., or 80° C. to 100° C. In some aspects, the deisopentanizer column operation condition during the separation of the first stream can include an operation gauge pressure of 1 bar to 15 bar or 1 bar to 10 bar or 2 bar to 8 bar or 3 bar to 6 bar. In some aspects, the deisopentanizer column operation condition during the separation of the first stream can include an overhead reflux to feed ratio of 0.5 to 12 or 1 to 10 or 2 to 8.8. In some aspects, the deisopentanizer column operation condition during the separation of the first stream can include an overhead boiling range temperature of 50° C. to 65° C., a reboiler range of 80° C. to 100° C., an operation gauge pressure of 3 to 6 bar, overhead reflux to feed ratio of 2 to 8.8 or any combination thereof. In some aspects, the deisopentanizer column can include 20 to 75, or 30 to 65, or 40 to 55, trays. In some aspects, in step (a) the third stream can be obtained as a bottom stream and the second stream can be obtained as a side stream from the deisopentanizer column. In some aspects the side stream can be a side-draw liquid stream. In some aspects the bottom stream can be a bottom-draw liquid stream. In some aspects, the second stream can contain 70 wt. % to 99.5 wt. %, or 70 wt. % to 99 wt. %, or 80 wt. % to 99 wt. % or 85 wt. % to 98 wt. %, of iso-pentane. In some aspects, the second stream can contain 0 wt. % to 30 wt. %, or 1 wt. % to 25 wt. %, or 2 wt. % to 20 wt. % or 5 wt. % to 15 wt. %, of n-pentane and neo-pentane. In some aspects, the second stream can contain less than 5 wt. %, or 0 wt. % to 5 wt. %, or 0.5 wt. % to 3 wt. %, of sulfur, where the sulfur is present as sulfur containing organosulfur compounds. The third stream can contain 90 wt. % to 100 wt. % or 90 wt. % to 99.5 wt. % or 95 wt. % to 99 wt. % n-pentane. The third stream can contain 0 wt. % to 10 wt. % or 0 wt. % to 5 wt. % neo-pentane. In some aspects, the third stream can contain, 90 wt. % to 99.5 wt. % n-pentane, and 0 wt. % to 10 wt. % neo-pentane. In some aspects, the first stream can further contain n-butane, and in step (a) the first stream can be separated to obtain the second stream, the third stream and a fifth stream containing n-butane. In some aspects, the fifth stream is obtained as a top stream from the deisopentanizer column. In some particular aspects, the first stream can contain 5 wt. % to 25 wt. % of n-butane. In some particular aspects, the fifth stream can contain 90 wt. % to 100 wt. % of n-butane. In some aspects, at least a portion of the iso-pentane of the second stream can be used as a blend stock for gasoline and/or blend stock for MTBE. In some aspects, a portion of the third stream is fed to the butane isomerization unit and a portion of the third stream is used a boiler fuel and/or for product blending.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions and systems of the invention can be used to achieve methods of the invention.

The following includes definitions of various terms and phrases used throughout this specification.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process and systems of the present invention can "comprise," "consist essentially of," or "consist of" particular ingredients, components, compositions, steps, etc. disclosed throughout the specification. With respect to the transitional phrase "consisting essentially of," in one non-limiting aspect, a basic and novel characteristic of the processes and the systems of the present invention are their abilities to process a pentanes stream containing iso-pentane, n-pentane, and neo-pentane from a DIB to obtain a stream containing iso-pentane, and a stream containing n-pentane, and neo-pentane, subjecting the stream containing n-pentane, and neo-pentane to a butane isomerization unit to obtain a stream containing iso-pentane, n-pentane and neo-pentane.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

Figure 1:
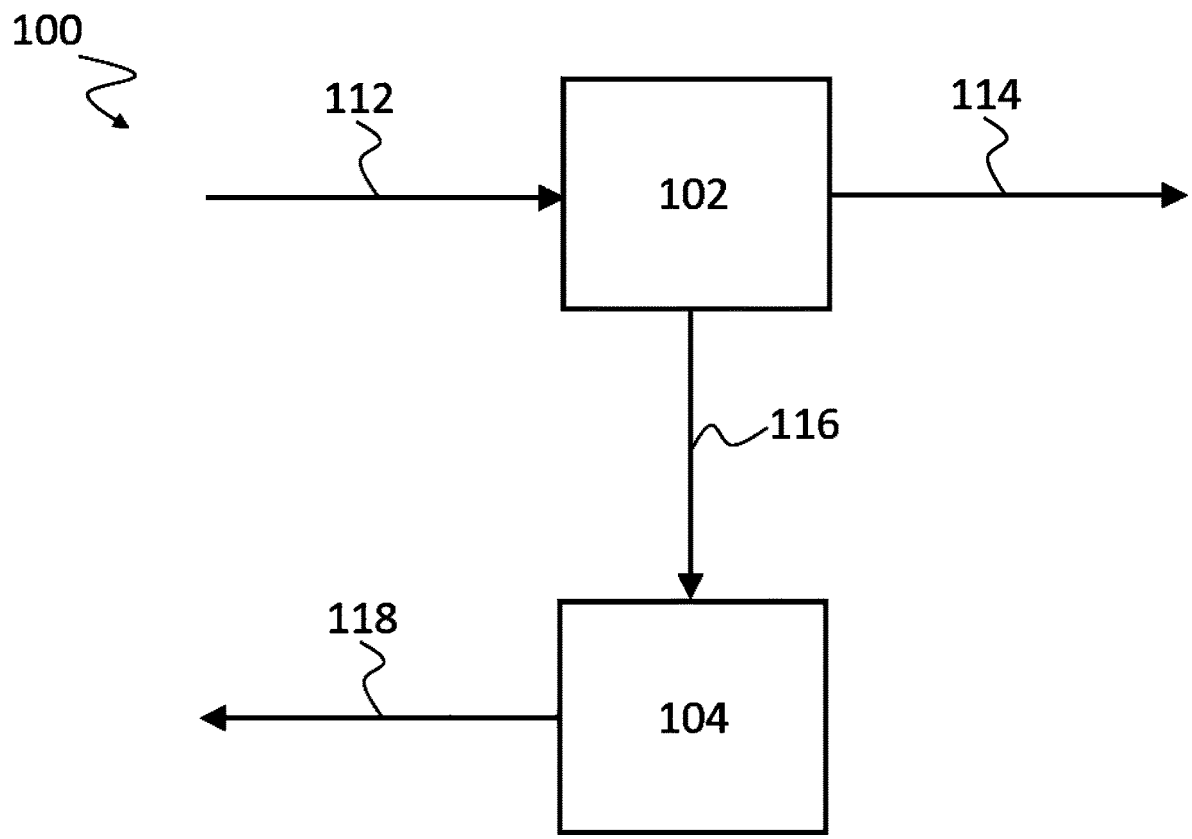
FIG. 1 is a schematic of one example of the present invention to process a pentanes stream from a DIB unit.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a solution to some of the aforementioned problems. The solution is premised on processing a pentanes stream containing iso-pentane, n-pentane, and neo-pentane from a DIB unit to recover iso-pentane, and producing additional iso-pentane from at least a portion of the resulting leftover stream. The leftover stream after iso-pentane recovery can contain n-pentane and neo-pentane. It was surprisingly found that recycling the left over stream to a butane isomerization unit can drive the equilibrium towards iso-pentane and convert n-pentane and/or neo-pentane to iso-pentane. The butane isomerization unit can be a butane isomerization unit of an iso-butane production process. The left over stream can be fed to the butane isomerization unit during a iso-butane production process.

These and other non-limiting aspects of the present invention are discussed in further detail in the following paragraphs with reference to the figures.

Referring to FIG. 1, one example of the system and process of the present invention for processing pentanes from a DIB unit is described. System 100 can include a separation column 102, and a butane isomerization unit 104. A first stream 112 can be fed to the separation column 102. The first stream can be obtained from a DIB unit (not shown). The first stream can contain iso-pentane, n-pentane, and neo-pentane. In the separation column 102 the first stream 112 can be separated into a second stream 114 containing iso-pentane and a third stream 116 containing n-pentane and neo-pentane. The third stream 116 can be fed to the butane isomerization unit 104. The butane isomerization unit 104 can contain an isomerization catalyst (not shown) and the isomerization catalyst can catalyze isomerization of n-pentane and/or neo-pentane to iso-pentane. A fourth stream 118 containing iso-pentane, n-pentane, and neo-pentane can be obtained from the butane isomerization unit 104.

Figure 2:
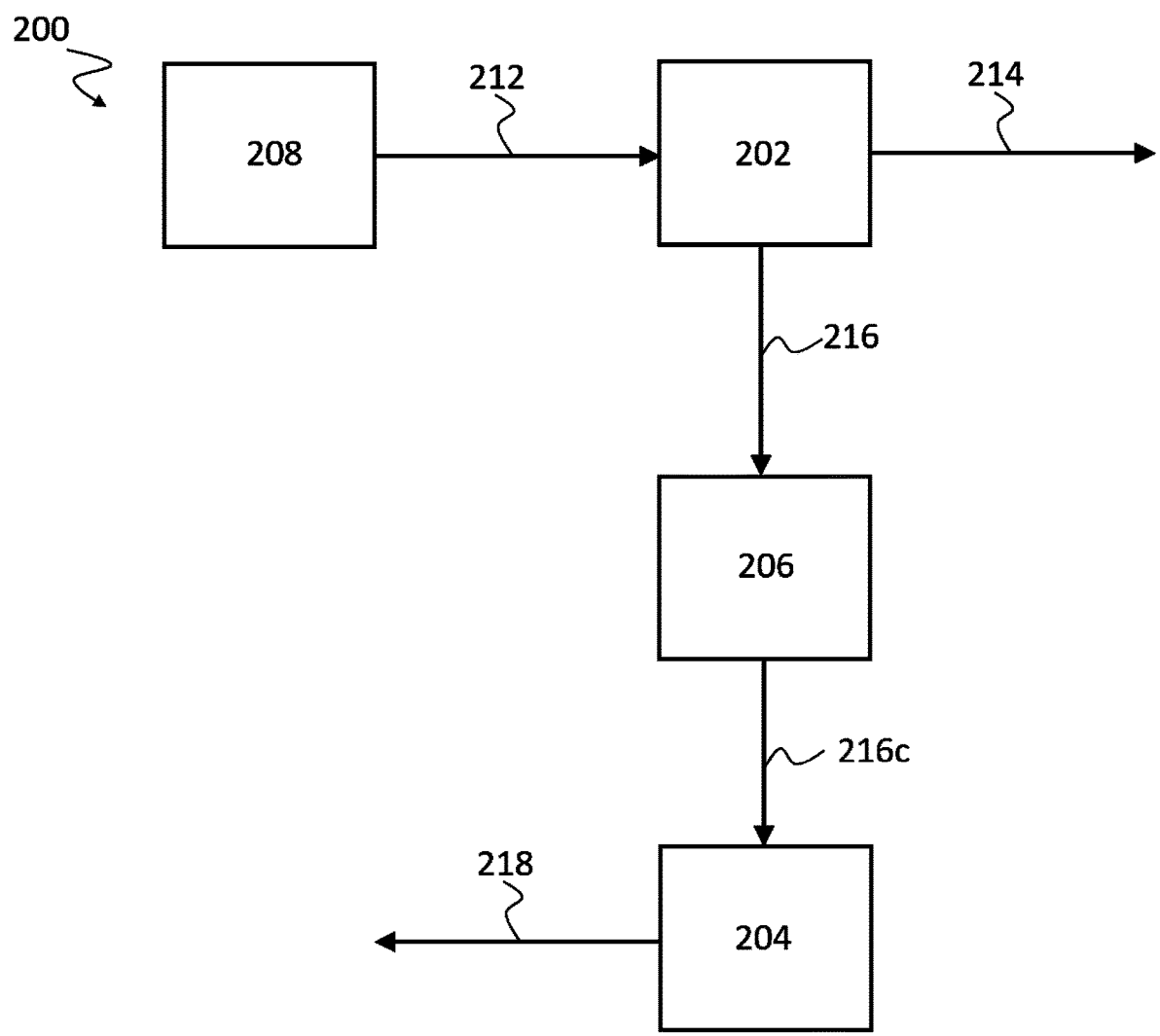
FIG. 2 is a schematic of a second example of the present invention to process a pentanes stream from a DIB unit.

Referring to FIG. 2, another example of the system and process of the present invention for processing pentanes from a DIB unit is described. System 200 can include a separation column 202, a butane isomerization unit 204, a desulfurization unit 206 and a DIB unit 208. A first stream 212 can be fed to the separation column 202. The first stream can be obtained from a DIB unit 208. The first stream can contain iso-pentane, n-pentane, and neo-pentane. In the separation column 202 the first stream 212 can be separated into a second stream 214 containing iso-pentane and a third stream 216 containing n-pentane and neo-pentane. The third stream 216 can be fed to the desulfurization unit 206. In the desulfurization unit 206 the third stream 216 can be desulfurized to obtain a desulfurized third stream 216c. The desulfurized third stream 216c can be fed to the butane isomerization unit 204. The butane isomerization unit 204 can contain an isomerization catalyst (not shown) and the isomerization catalyst can catalyze isomerization of n-pentane and/or neo-pentane to iso-pentane. A fourth stream 218 containing iso-pentane, n-pentane, and neo-pentane can be obtained from the butane isomerization unit 204.

Figure 3:
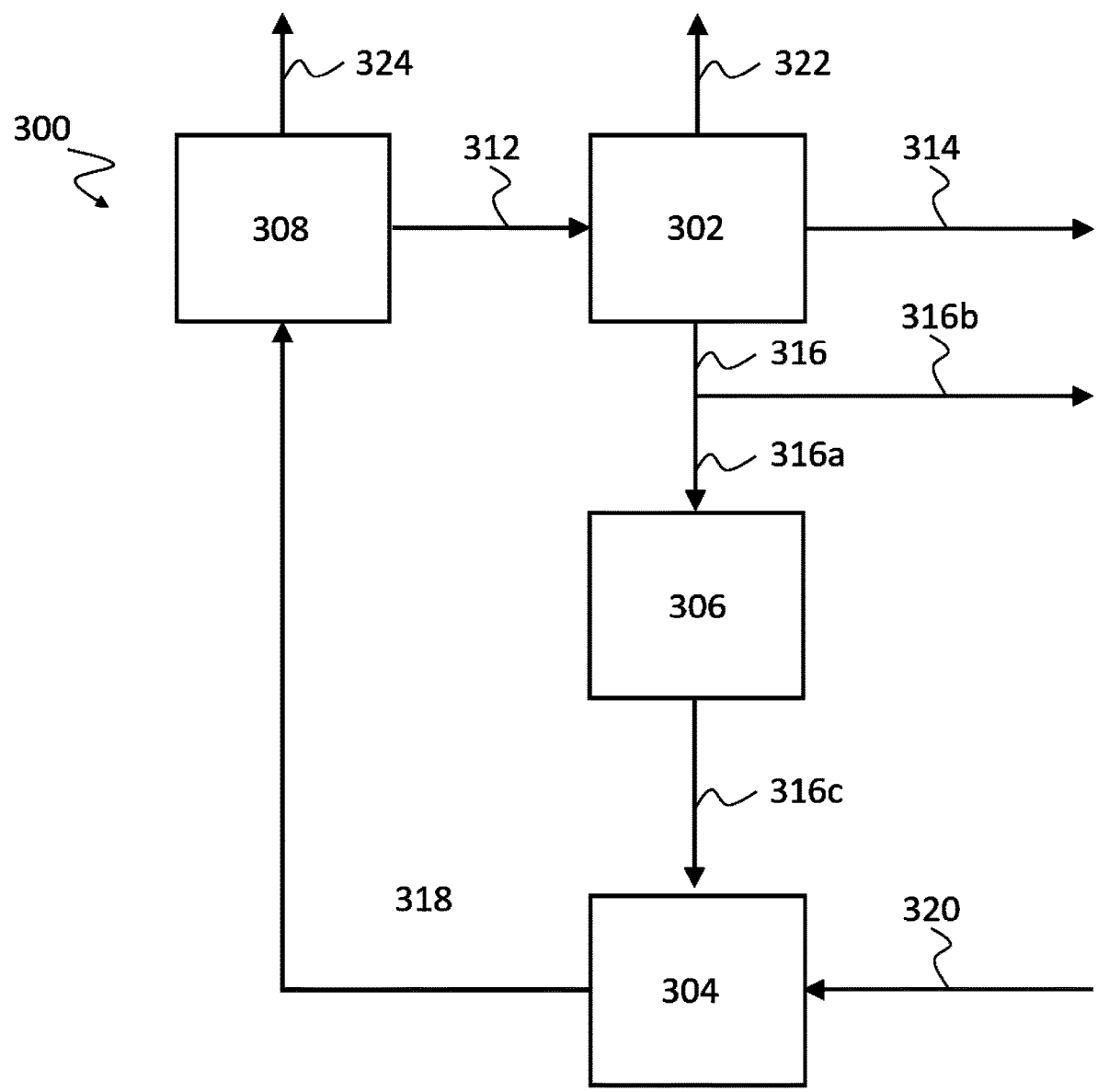
FIG. 3 is a schematic of a third example of the present invention to process a pentanes stream from a DIB unit.

Referring to FIG. 3, another example of the system and process of the present invention for processing pentanes from a DIB unit is described. System 300 can include a separation column 302, a butane isomerization unit 304, a desulfurization unit 306 and a DIB unit 308. A first stream 312 can be fed to the separation column 302. The first stream 312 can contain n-butane, iso-pentane, n-pentane, and neo-pentane. The first stream 312 can be obtained from the DIB unit 308. In the separation column 302 the first stream 312 can be separated into a second stream 314 containing iso-pentane, a third stream 316 containing n-pentane and neo-pentane and a fifth stream 322 containing n-butane. A portion 316a of the third stream can be fed to the desulfurization unit 306. In the desulfurization unit 306 the stream 316a can be desulfurized to obtain a desulfurized third stream 316c. The desulfurized third stream 316c can be fed to the butane isomerization unit 304. A portion of the third stream 316b can be used as boiler fuel and/or product blending. A feed stream 320 containing n-butane can be fed to the butane isomerization unit 304. In some aspects, the feed stream 320 can further include iso-butane, n-pentane, iso-pentane, and neo-pentane. In some aspects, the desulfurized third stream 316c and the feed stream 320 can be fed to the butane isomerization unit 304 as separate feeds. In some aspects, the desulfurized third stream 316c and the feed stream 320 can be fed to the butane isomerization unit 304 as a combined feed (not shown). The feed stream 320 can be desulfurized (not shown) and then fed to the butane isomerization unit 304. The butane isomerization unit 304 can contain an isomerization catalyst (not shown) and the isomerization catalyst can catalyze isomerization of n-pentane and/or neo-pentane to iso-pentane and n-butane to iso-butane. A fourth stream 318 containing n-butane, iso-butane, iso-pentane, n-pentane, and neo-pentane can be obtained from the butane isomerization unit 304. The fourth stream can be fed to the DIB unit 308. In the DIB unit 308 the fourth stream can be separated to obtain the first stream 312 and a sixth stream 324 containing iso-butane.

Figure 4:
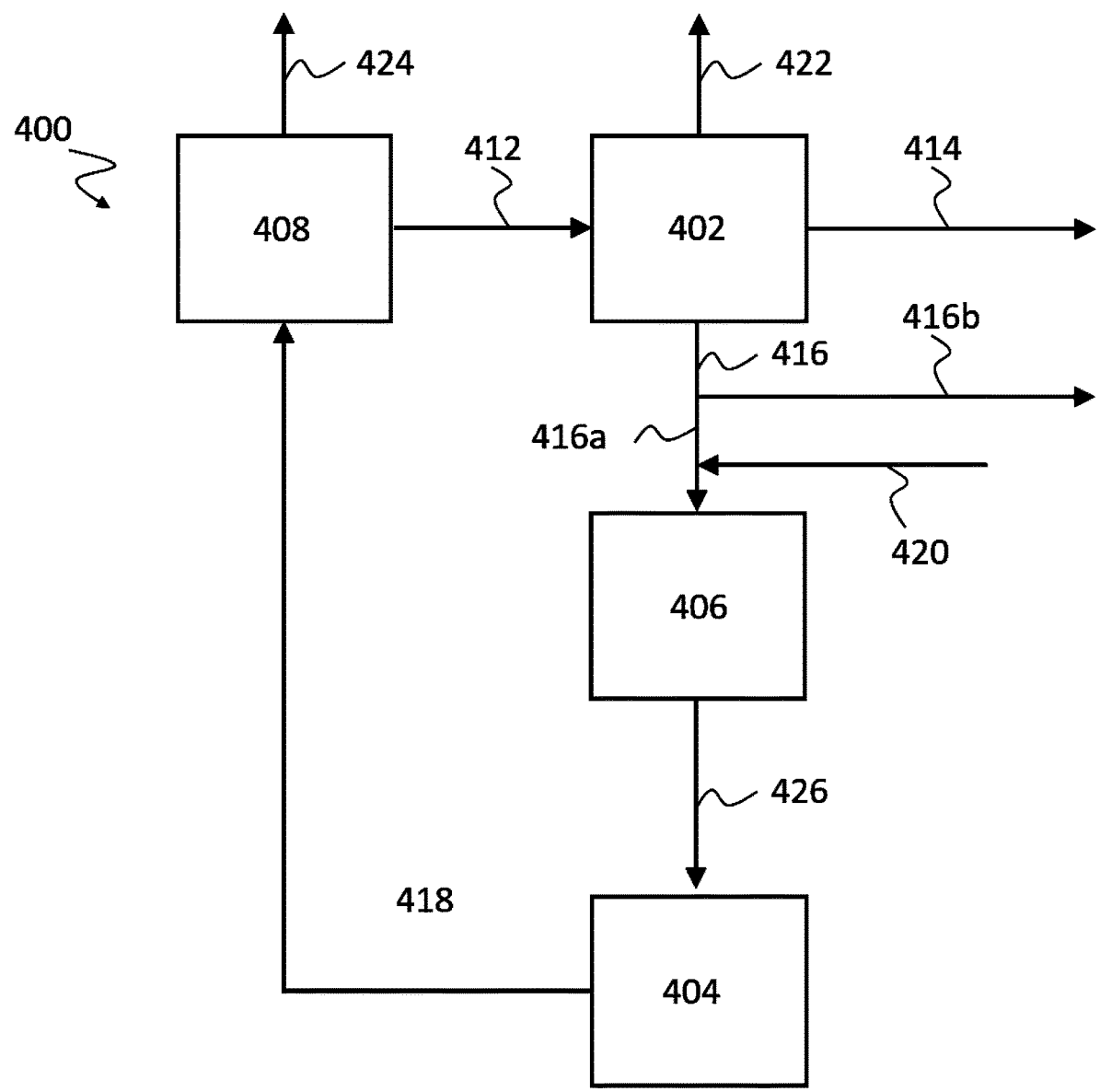
FIG. 4 is a schematic of a fourth example of the present invention to process a pentanes stream from a DIB unit.

Referring to FIG. 4, another example of the system and process of the present invention for processing pentanes from a DIB unit is described. System 400 can include a separation column 402, a butane isomerization unit 404, a desulfurization unit 406 and a DIB unit 408. A first stream 412 can be fed to the separation column 402. The first stream 412 can contain n-butane, iso-pentane, n-pentane, and neo-pentane. The first stream 412 can be obtained from the DIB unit 408. In the separation column 402 the first stream 412 can be separated into a second stream 414 containing iso-pentane, a third stream 416 containing n-pentane and neo-pentane and a fifth stream 422 containing n-butane. A portion 416a of the third stream can be fed to the desulfurization unit 406. A feed stream 420 containing n-butane can be fed to the desulfurization unit 406. In some aspects, the feed stream 420 can further include iso-butane, n-pentane, iso-pentane and neo-pentane. In some aspects, the stream 416a and the feed stream 420 can be fed to the desulfurization unit 406 as separate feeds (not shown). In some aspects, the stream 416a and the feed stream 420 can be fed to the desulfurization unit 406 as a combined feed. In the desulfurization unit 406 the feed stream 420 and the stream 416a can be desulfurized to obtain a desulfurized combined stream 426. The desulfurized combined stream 426 can be fed to the butane isomerization unit 404. A portion of the third stream 416b can be used as boiler fuel and/or product blending. The butane isomerization unit 404 can contain an isomerization catalyst (not shown) and the isomerization catalyst can catalyze isomerization of n-pentane and/or neo-pentane to iso-pentane and n-butane to iso-butane. A fourth stream 418 containing n-butane, iso-butane, iso-pentane, n-pentane, and neo-pentane can be obtained from the butane isomerization unit 404. The fourth stream can be fed to the DIB unit 408. In the DIB unit 408 the fourth stream can be separated to obtain the first stream 412 and a sixth stream 424 containing iso-butane.

Figure 5:
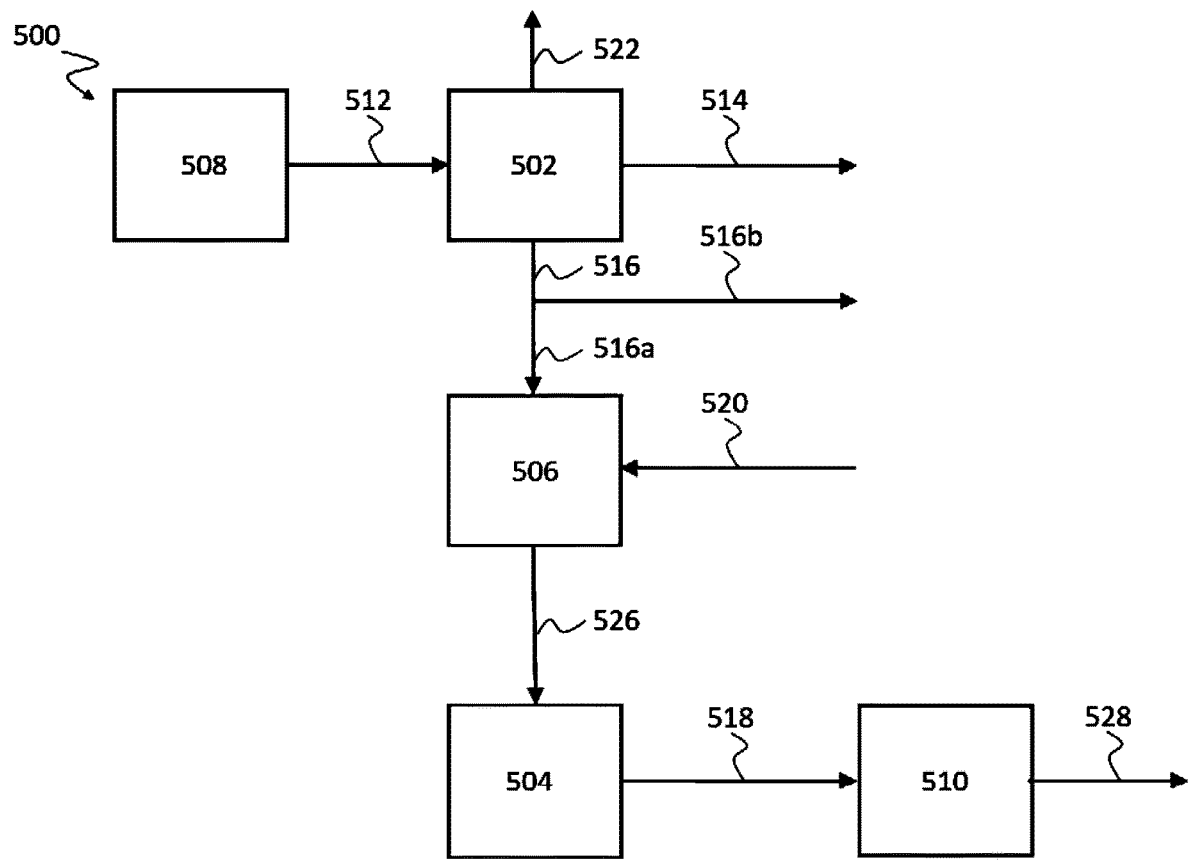
FIG. 5 is a schematic of a fifth example of the present invention to process a pentanes stream from a DIB unit.

Referring to FIG. 5, another example of the system and process of the present invention for processing pentanes from a DIB unit is described. System 500 can include a separation column 502, a butane isomerization unit 504, a desulfurization unit 506 and DIB units 508 and 510. A first stream 512 can be fed to the separation column 502. The first stream 512 can contain n-butane, iso-pentane, n-pentane, and neo-pentane. The first stream 512 can be obtained from the DIB unit 508. In the separation column 502 the first stream 512 can be separated into a second stream 514 containing iso-pentane, a third stream 516 containing n-pentane and neo-pentane and a fifth stream 522 containing n-butane. A portion 516a of the third stream can be fed to the desulfurization unit 506. A feed stream 520 containing n-butane can be fed to the desulfurization unit 506. In some aspects, the feed stream 520 can further include iso-butane, n-pentane, iso-pentane, and neo-pentane. In some aspects, the stream 516a and the feed stream 520 can be fed to the desulfurization unit 506 as separate feeds. In some aspects, stream 516a and the feed stream 520 can be fed to the desulfurization unit 506 as a combined feed (not shown). In the desulfurization unit 506 the feed stream 520 and the stream 516a can be desulfurized to obtain a desulfurized combined stream 526. The desulfurized combined stream 526 can be fed to the butane isomerization unit 504. A portion of the third stream 516b can be used as boiler fuel and/or product blending. The butane isomerization unit 504 can contain an isomerization catalyst (not shown) and the isomerization catalyst can catalyze isomerization of n-pentane and/or neo-pentane to iso-pentane and n-butane to iso-butane. A fourth stream 518 containing n-butane, iso-butane, iso-pentane, n-pentane, and neo-pentane can be obtained from the butane isomerization unit 504. The fourth stream can be fed to the DIB unit 510. In the DIB unit 510 the fourth stream 518 can be separated to obtain a seventh stream 528 containing iso-pentane, n-pentane and neo-pentane. The pentanes from the seventh stream 528 can be processed according to any examples described herein.

The first stream 112, 212, 312, 412, 512 can contain (1) 30 wt. % to 70 wt. % or at least any one of, equal to any one of, or between any two of 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %, 61 wt. %, 62 wt. %, 63 wt. %, 64 wt. %, 65 wt. %, 66 wt. %, 67 wt. %, 68 wt. %, 69 wt. %, and 70 wt. % of isopentane; (2) 15 wt. % to 35 wt. % or at least any one of, equal to any one of, or between any two of 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, and 35 wt. % of n-pentane; (3) 1 wt. % to 15 wt. % or at least any one of, equal to any one of, or between any two of 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, and 15 wt. %, of neo-pentane; or (4) 5 wt. % to 25 wt. % or at least any one of, equal to any one of, or between any two of 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, and 25 wt. %, of n-butane; or any combination thereof.

The second stream 114, 214, 314, 414, 514 can contain 70 wt. % to 99.5 wt. % or at least any one of, equal to any one of, or between any two of 70 wt. %, 71 wt. %, 72 wt. %, 73 wt. %, 74 wt. %, 75 wt. %, 76 wt. %, 77 wt. %, 78 wt. %, 79 wt. %, 80 wt. %, 81 wt. %, 82 wt. %, 83 wt. %, 84 wt. %, 85 wt. %, 86 wt. %, 87 wt. %, 88 wt. %, 89 wt. %, 90 wt. %, 91 wt. %, 92 wt. %, 93 wt. %, 94 wt. %, 95 wt. %, 96 wt. %, 97 wt. %, 98 wt. %, 99 wt. %, and 99.5 wt. % of isopentane. The total wt. % of n-pentane and neo-pentane in the second stream 114, 214, 314, 414, 514 can be less than 30 wt. %. In some aspects, the total wt. % of n-pentane and neo-pentane in the second stream 114, 214, 314, 414, 514 can be 0 wt. % to 30 wt. %, or at least any one of, equal to any one of, or between any two of 0 wt. %, 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, and 30 wt. %. The second stream 114, 214, 314, 414, 514 can contain less than 5 wt. % to sulfur. In some aspects the second stream 114, 214, 314, 414, 514 can contain 0 wt. % to less than 5 wt. % or less than any one of, equal to any one of, or between any two 0 wt. %, 0.1 wt. %, 0.5 wt. % 1 wt. %, 1.5 wt. % 2 wt. %, 2.5 wt. % 3 wt. %, 3.5 wt. % 4 wt. %, 4.5 wt. % and 5 wt. % of sulfur. The sulfur in the second stream 114, 214, 314, 414, 514 can be present as organosulfur compounds. In some aspects, the iso-pentane of the second stream can be used as solvents, blend stock for gasoline, or blend stock for MTBE, or any combination thereof.

The third stream 116, 216, 316, 416, 516, 316a, 316b, 416a, 416b, 516a, 516b, can contain 90 wt. % to 99.5 wt. % or at least any one of, equal to any one of, or between any two of 90 wt. %, 91 wt. %, 92 wt. %, 93 wt. %, 94 wt. %, 95 wt. %, 96 wt. %, 97 wt. %, 98 wt. %, 99 wt. %, and 99.5 wt. % of n-pentane; and/or 0 wt. % to 10 wt. % or at least any one of, equal to any one of, or between any two of 0 wt. %, 0.1 wt. %, 0.5 wt. %, 1 wt. %, 2 wt. %, 3 wt. %, 4 wt.

%, 5 wt. %, 6 wt. %, 7 wt. %, 8 wt. %, 9 wt. %, and 10 wt. %, % of neo-pentane. In some aspects, the third stream 116, 216, 316, 416, 516, 316a, 316b, 416a, 416b, 516a, 516b can further contain hexanes.

The fourth stream 118, 218, 318, 418, 518 can contain 0.5 wt. % to 65 wt. % or at least any one of, equal to any one of, or between any two of 0.5 wt. %, 1 wt. %, 5 wt. %, 10 wt. %, 15 wt. %, 20 wt. %, 25 wt. %, 30 wt. %, 35 wt. %, 40 wt. %, 45 wt. %, 50 wt. %, 55 wt. %, and 65 wt. % of iso-pentane, 0.5 wt. % to 30 wt. % or at least any one of, equal to any one of, or between any two of 0.5 wt. %, 1 wt. %, 5 wt. %, 10 wt. %, 15 wt. %, 20 wt. %, 25 wt. %, and 30 wt. % of n-pentane and 0.5 wt. % to 5 wt. % or at least any one of, equal to any one of, or between any two of 0.5 wt. %, 1 wt. %, 2 wt. %, 3 wt. %, 4 wt. %, and 5 wt. %, of neo-pentane. In some aspects, the fourth stream 318, 418, 518 can further contain 40 wt. % to 65 wt. % or at least any one of, equal to any one of, or between any two of 40 wt. %, 45 wt. %, 50 wt. %, 55 wt. %, and 65 wt. % of iso-butane, 30 wt. % to 50 wt. % or at least any one of, equal to any one of, or between any two of 30 wt. %, 35 wt. %, 40 wt. %, 45 wt. %, 50 wt. %, 55 wt. %, and 50 wt. % of n-butane.

The fifth stream 322, 422, 522, can include 90 wt. % to 100 wt. % or at least any one of, equal to any one of, or between any two of 90 wt. %, 91 wt. %, 92 wt. %, 93 wt. %, 94 wt. %, 95 wt. %, 96 wt. %, 97 wt. %, 98 wt. %, 99 wt. %, 99.5 wt. % and 100 wt. % of n-butane.

The seventh stream 528 can contain (1) 30 wt. % to 70 wt. % or at least any one of, equal to any one of, or between any two of 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %, 61 wt. %, 62 wt. %, 63 wt. %, 64 wt. %, 65 wt. %, 66 wt. %, 67 wt. %, 68 wt. %, 69 wt. %, and 70 wt. % of isopentane; (2) 15 wt. % to 35 wt. % or at least any one of, equal to any one of, or between any two of 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, and 35 wt. % of n-pentane; (3) 1 wt. % to 15 wt. % or at least any one of, equal to any one of, or between any two of 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, and 15 wt. %, of neo-pentane; or (4) 5 wt. % to 25 wt. % or at least any one of, equal to any one of, or between any two of 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, and 25 wt. %, of n-butane; or any combination thereof.

The feed stream 320, 420, 520, can contain 55 wt. % to 85 wt. % or at least any one of, equal to any one of, or between any two of 55 wt. %, 56 wt. %, 57 wt. %, 58 wt. %, 59 wt. %, 60 wt. %, 61 wt. %, 62 wt. %, 63 wt. %, 64 wt. %, 65 wt. %, 66 wt. %, 67 wt. %, 68 wt. %, 69 wt. %, 70 wt. %, 71 wt. %, 72 wt. %, 73 wt. %, 74 wt. %, 75 wt. %, 76 wt. %, 77 wt. %, 78 wt. %, 79 wt. %, 80 wt. %, 81 wt. %, 82 wt. %, 83 wt. %, 84 wt. %, and 85 wt. % of n-butane. In some aspects, the feed stream 320, 420, 520 can further contain (1) 12 wt. % to 35 wt. % or at least any one of, equal to any one of, or between any two of 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, and 35 wt. % of iso-butane; (2) 0.01 wt. % to 3 wt. % or at least any one of, equal to any one of, or between any two of 0.01 wt. %, 0.1 wt. %, 0.5 wt. %, 1 wt. %, 1.5 wt. %, 2 wt. %, 2.5 wt. % and 3 wt. % of iso-pentane; (3) 0.01 wt. % to 5 wt. % or at least any one of, equal to any one of, or between any two of 0.01 wt. %, 0.1 wt. %, 0.5 wt. %, 1 wt. %, 1.5 wt. %, 2 wt. %, 2.5 wt. %, 3 wt. %, 3.5 wt. % 4 wt. %, 4.5 wt. % and 5 wt. % of n-pentane; or (4) 0.01 wt. % to 3 wt. % or at least any one of, equal to any one of, or between any two of 0.01 wt. %, 0.1 wt. %, 0.5 wt. %, 1 wt. %, 1.5 wt. %, 2 wt. %, 2.5 wt. % and 3 wt. % of neo-pentane or any combination thereof.

Generally, in the separation column 102, 202, 302, 402, 502 iso-pentane can be separated from other hydrocarbons, such as n-pentane, neo-pentane, and n-butane. In some aspects, the separation column 102, 202, 302, 402, 502 can be a distillation column. In some aspects, the separation column 102, 202, 302, 402, 502 can be a deisopentanizer column. In some aspects, the separation column 102, 202, 302, 402, 502 operation condition during the separation of the first stream 112, 212, 312, 412, 512 can include (1) an overhead boiling range temperature of 30° C. to 85° C., or at least any one of, equal to any one of, or between any two of 30° C., 32° C., 34° C., 36° C., 38° C., 40° C., 42° C., 44° C., 46° C., 48° C., 50° C., 52° C., 54° C., 56° C., 58° C., 60° C., 62° C., 64° C., 65° C., 66° C., 68° C., 70° C., 72° C., 74° C., 75° C., 76° C., 78° C., 80° C., 82° C., 84° C., and 85° C.; (2) a reboiler range of 70° C. to 120° C., or at least any one of, equal to any one of, or between any two of 70° C., 72° C., 74° C., 76° C., 78° C., 80° C., 82° C., 84° C., 86° C., 88° C., 90° C., 92° C., 94° C., 96° C., 98° C., 100° C., 102° C., 104° C., 106° C., 108° C., 100° C., 102° C., 104° C., 106° C., 108° C., 110° C., 112° C., 114° C., 116° C., 118° C., and 120° C.; (3) an operation gauge pressure of 1 bar to 15 bar or at least any one of, equal to any one of, or between any two of 1 bar, 2 bar, 3 bar, 4 bar, 5 bar, 6 bar, 7 bar, 8 bar, 9 bar, 10 bar, 11 bar, 12 bar, 13 bar, 14 bar, and 15 bar; or (4) an overhead reflux to feed ratio of 0.5 to 12 or at least any one of, equal to any one of, or between any two of 0.5, 1, 2, 3, 4, 5, 6, 7, 8, 8.8, 9 and 10 or any combination thereof. In some aspects, the separation column 102, 202, 302, 402, 502 can include 20 to 75 or at least any one of, equal to any one of, or between any two of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 of trays. The second stream 114, 214, 314, 414, 514 can be obtained as a side stream from the separation column 102, 202, 302, 402, 502. The third stream 116 can be obtained as a bottom stream from the separation column 102, 202, 302, 402, 502. The fifth stream 322, 422 and 522 can be obtained as a top stream from the from the separation column 302, 402, 502.

Generally, in the butane isomerization unit 104, 204, 304, 404, 504 n-butane can be isomerized to iso-butane and n-pentane and/or neo-pentane can be isomerized to iso-pentane. In some aspects, the butane isomerization unit 104, 204, 304, 404, 504 can be an butane isomerization unit used for a butane isomerization process, such as process for preparing iso-butane from n-butane. The butane isomerization unit 104, 204, 304, 404, 504 operation condition to obtain the fourth stream can include (1) a temperature of 130° C. to 300° C. or at least any one of, equal to any one of, or between any two of 130° C., 140° C., 150° C., 160° C., 170° C., 180° C., 200° C., 210° C., 220° C., 230° C., 240° C., 250° C., 260° C., 270° C., 280° C., 290° C., and 300° C.; (2) a pressure of 10 bar to 40 bar or at least any one of, equal to any one of, or between any two of 10 bar, 15 bar, 20 bar, 25 bar, 30 bar, 35 bar and 40 bar; (3) a WHSV of 0.5 $h^{-1}$ to 10 $h^{-1}$ or at least any one of, equal to any one of, or between any two of 1 $h^{-1}$, 2 $h^{-1}$, 3 $h^{-1}$, 4 $h^{-1}$, 5 $h^{-1}$, 6 $h^{-1}$, 7 $h^{-1}$, 8 $h^{-1}$, 9 $h^{-1}$, and 10 $h^{-1}$ or any combination thereof. In some aspects, temperature at an inlet for the streams 116, 216c, 316c, 426, 526 to the butane isomerization unit can be 55° C. to 85° C. and temperature at the butane isomerization unit can be raised to about 130° C. to 300° C., start of the run (SOR) to end of run (EOR)

In the desulfurization unit 206, 306, 406, 506 hydrocarbons and/or hydrocarbons streams can be desulfurized. The desulfurizing process can include absorption and removing of sulfur containing compounds from the streams 216, 316a, 416a, 420, 516a, 520 by an adsorbent. In some aspects, the adsorbent can be zeolite 13X and/or activated charcoal. In some aspects, the desulfurization unit 206, 306, 406, 506 can contain fixed beds containing zeolite 13X molecular sieve and/or an activated charcoal and the desulfurization process can include passing the streams 216, 316a, 416a, 420, 516a, 520 over and/or through the fixed bed at an ambient temperature or/and a pressure of 8 to 25 bar, or at least any one of, equal to any one of, or between any two of 8, 9, 10, 11, 12, 13, 14, 15, 16, 17, 18, 19, 20, 21, 22, 23, 24 bar and 25 bar. A spent adsorbent can be formed by absorption of the sulfur containing compounds by the adsorbent. In some aspects, the adsorbent can be regenerated from the spent adsorbent. In some aspects, the regeneration process can include passing a gaseous stream containing $N_2$, $H_2$ and/or sulfur free isobutane over and/or through a bed containing spent 13X and/or spent activated charcoal at a temperature 250° C. to 450° C. and/or a pressure 0.5 bar to 10 bar, 1 bar to 5 bar or 2 bar to 3 bar. In some aspects, the system 200, 300, 400, 500 can include multiple desulfurization units (not shown). The desulfurization in an online desulfurization unit and regeneration in an offline second desulfurization unit can be performed simultaneously. At a point when regeneration of the adsorbent in the desulfurization unit becomes necessary, the online desulfurization unit can be taken offline for adsorbent regeneration and offline second desulfurization unit with regenerated adsorbent can be brought online for desulfurization. This arrangement provides a process for continuous desulfurization, as well as adsorbent regeneration. In some aspects, the desulfurization unit 206, 306, 406, 506 can include a sulfur removal drier. In some aspects, the feed stream 420, 520 can further contain 1 to 80 ppm or 1 to 35 ppm of sulfur containing compounds. The some aspects, the sulfur containing compounds can be $H_2S$, mercaptans such as methyl, ethyl, and propyl mercaptans, carbonyl sulfide, di methyl di sulfide, di ethyl di sulfide, di methyl sulfide, di ethyl sulfide, or any combination thereof. In some aspects, after the desulfurization process, sulfur containing compounds content in the streams 216c, 316c, 426, 526 exiting the desulfurization unit 206, 306, 406, 506 can be less than 5 ppm, or less than 3 ppm, such as 0 to 3 ppm or 1 ppm to 3 ppm or 2 ppm to 3 ppm.

In some aspects, the DIB unit 208, 308, 408, 508, 510 can include a distillation column. In some particular aspect, the distillation column of the DIB unit 208, 308, 408, 508, 510 can be a DIB column. Generally, the DIB column can separate iso-butane, n-butane, and pentanes. In some aspects, the DIB column operation condition during production of the first stream 112, 212, 312, 412, 512 and/or seventh stream 528 can include (1) an temperature of 30° C. to 80° C., or at least any one of, equal to any one of, or between any two of 30° C., 32° C., 34° C., 36° C., 38° C., 40° C., 42° C., 44° C., 46° C., 48° C., 50° C., 52° C., 54° C., 56° C., 58° C., 60° C., 62° C., 64° C., 66° C., 68° C., 70° C., 72° C., 74° C., 76° C., 78° C., and 80° C.; (2) a reboiler range of 70° C. to 120° C., or at least any one of, equal to any one of, or between any two of 70° C., 72° C., 74° C., 76° C., 78° C., 80° C., 82° C., 84° C., 86° C., 88° C., 90° C., 92° C., 94° C., 96° C., 98° C., 100° C., 102° C., 104° C., 106° C., 108° C., 100° C., 102° C., 104° C., 106° C., 108° C., 110° C., 112° C., 114° C., 116° C., 118° C., and 120° C.; (3) an operation gauge pressure of 0.1 bar to 10 bar or at least any one of, equal to any one of, or between any two of 0.1 bar, 0.2 bar, 0.5 bar, 1 bar, 2 bar, 3 bar, 4 bar, 5 bar, 6 bar, 7 bar, 8 bar, 9 bar, and 10 bar; or (4) an overhead reflux to feed ratio of 0.5 to 12 or at least any one of, equal to any one of, or between any two of 0.5, 1, 2, 3, 4, 5, 6, 7, 8, 8.8, 9 and 10 or any combination thereof. In some aspects, the DIB column can include 20 to 75 or at least any one of, equal to any one of, or between any two of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 of trays.

In FIGS. 1-5 the reactors, units and/or zones can include one or more heating and/or cooling devices (e.g., insulation, electrical heaters, jacketed heat exchangers in the wall) and/or controllers (e.g., computers, flow valves, automated values, etc.) that can be used to control the reaction temperature and pressure of the reaction mixture. While only one unit or zone is shown, it should be understood that multiple reactors or zones can be housed in one unit or a plurality of reactors housed in one heat transfer unit. In some aspects, the reactor can be a fixed bed reactor, moving bed, trickle-bed reactor, rotating bed reactor, slurry reactors or fluidized bed reactor.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Process for Process Pentanes from a DIB Unit

A pentanes stream from a DIB unit was processed according to the Example of FIG. 4. A feed stream containing methane, ethane, propane, n-butane, iso-butane, n-pentane, iso-pentane, and neo-pentane was desulfurized. The resulting desulfurized stream was then fed to a butane isomerization unit. The resulting stream from the butane isomerization unit was fed to a DIB column. The DIB column used was a sieve column with multiple downcomers designed for high liquid loading over the weir, (15-20 gpm/inch weir length). A pentanes streams was obtained as a bottom stream of the DIB column. The pentanes stream was fed to a deisopentanizer column. The deisopentanizer column used was a single pas sieve tray column with a side draw fitting.

An iso-pentane containing stream, a n-pentane and neo-pentane containing stream, and a n-butane containing stream was obtained from the deisopentanizer column. A portion of the n-pentane and neo-pentane containing stream was combined with the feed stream, was desulfurized and was then fed to the butane isomerization unit. 13× molecular sieve was used desulfurization. Desulfurization was performed at 30° C. to 45° C. and 4 to 15 bar. Additional iso-pentane was produced in the butane isomerization unit from the n-pentane and/or neo-pentane. Composition of the different streams are provided in table 1

TABLE 1

Mass balance

|  | Feed Stream | Pentanes Stream | n-butane stream | Iso-pentane stream | n-pentane and neo pentane stream |
|---|---|---|---|---|---|
| methane (Kg/hr) | 136.50 |  |  |  |  |
| ethane (Kg/hr) | 21.00 |  |  |  |  |
| propane (Kg/hr) | 1459.50 |  |  |  |  |
| iso-butane (Kg/hr) | 25767.00 |  |  |  |  |
| n-butane (Kg/hr) | 77133.00 | 400.00 | 400.00 |  |  |
| n-pentane (Kg/hr) | 580.28 | 674.41 |  | 0.00 | 674.71 |
| n-pentane + neo-pentane (Kg/hr) | 1547.42 | 200.00 |  | 200.00 |  |
| Isopentane | 96.71 | 1350.00 |  | 1350.00 |  |
| Total | 106741.41 | 2624.41 | 400.00 | 1550.00 | 674.71 |

In the context of the present invention, at least the following 20 embodiments are described. Embodiment 1 is a method for processing pentanes obtained from a DIB unit, the method includes (a) separating a first stream containing pentanes in a separation column to obtain a second stream containing iso-pentane and a third stream containing n-pentane and neo-pentane, and (b) subjecting the third stream to a butane isomerization unit producing a fourth stream containing iso-pentane, n-pentane, and neo-pentane. Embodiment 2 is directed to embodiment 1, wherein the third stream is desulfurized prior to subjecting the third stream to the butane isomerization unit. Embodiment 3 is directed to embodiment 2, wherein the desulfurization process includes absorption and removing of sulfur containing compounds from the third stream by an adsorbent. Embodiment 4 is directed to any one of embodiments, 1 to 3, wherein in the butane isomerization unit the third stream is contacted with a isomerization catalyst under conditions including a temperature of 130° C. to 300° C., a pressure 10 to 40 bar, a WHSV 0.5 h$^{-1}$ to 10$^{-1}$ or any combination thereof. Embodiment 5 is directed to embodiment 4, the isomerization catalyst is a platinum chlorinated alumina (Pt/Al$_2$O$_3$—Cl) catalyst, a platinum zirconia sulfate catalyst (Pt/ZrO$_2$—SO$_4$) and/or an iso shape selective zeolites. Embodiment 6 is directed to any one of embodiments 1 to 5, wherein a feed stream containing n-butane is fed to the butane isomerization unit and the fourth stream further contains n-butane and iso-butane. Embodiment 7 is directed to embodiment 6, wherein the third stream and the feed stream is fed to the butane isomerization unit as separate feeds. Embodiment 8 is directed to embodiment 6, wherein the third stream and the feed stream is fed to the butane isomerization unit as a combined feed. Embodiment 9 is directed to any one of embodiments 1 to 8, wherein the fourth stream is subjected to the DIB unit. Embodiment 10 is directed to any one of embodiments 1 to 9, wherein the DIB unit contains a DIB column and the DIB column operation condition to obtain the first stream includes a temperature of 50 to 60° C., a reboiler range of 90 to 100° C., or an operation gauge pressure of 1 to 5 bar, or any combination thereof. Embodiment 11 is directed to any one of embodiments 1 to 10, wherein the first stream contains 30 wt. % to 70 wt. % iso-pentane, 15 wt. % to 35 wt. % n-pentane, and 1 wt. % to 15 wt. % neo-pentane. Embodiment 12 is directed to any one of embodiments 1 to 11, wherein during the separation of the first stream in step (a) the separation column operation conditions includes an overhead boiling range temperature of 50° C. to 65° C., a reboiler range of 80° C. to 100° C., or an operation gauge pressure of 3 to 6 bar, or any combination thereof. Embodiment 13 is directed to any one of embodiments 1 to 12, wherein in step (a) the third stream is obtained as a bottom stream and the second stream is obtained as a side stream from the separation column. Embodiment 14 is directed to any one of embodiments 1 to 13, wherein the second stream contains 70 wt. % to 98 wt. % of iso-pentane. Embodiment 15 is directed to any one of embodiments 1 to 14, wherein the second stream contains 0 wt. % to 30 wt. % of n-pentane and neo-pentane. Embodiment 16 is directed to any one of embodiments 1 to 15, wherein the second stream contains less than 5 wt. %, such as 0 wt. % to 5 wt. % % of sulfur. Embodiment 17 is directed to any one of embodiments 1 to 16, wherein the third stream contains 90 wt. % to 99.5 wt. % n-pentane and 0 wt. % to 10 wt. % neo-pentane. Embodiment 18 is directed to any one of embodiments 1 to 17, wherein the first stream further comprises n-butane, and in step (a) the first stream is separated to obtain the second stream, the third stream and a fifth stream comprising n-butane. Embodiment 19 is directed to embodiment 18, wherein in step (a) the fifth stream is obtained as a top stream from the separation column. Embodiment 20 is directed to any one of embodiments 1 to 19, wherein the iso-pentane of second stream is used as a blend stock for gasoline and/or blend stock for MTBE.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A method for processing pentanes obtained from a de-isobutanizer (DIB) unit, the method comprising:
    (a) separating a first stream comprising pentanes in a separation column to obtain a second stream comprising iso-pentane and a third stream comprising n-pentane and neo-pentane; and
    (b) subjecting the third stream to a butane isomerization unit producing a fourth stream comprising iso-pentane, n-pentane, and neo-pentane.

2. The method of claim 1, wherein the third stream is desulfurized prior to subjecting the third stream to the butane isomerization unit.

3. The method of claim 2, wherein the desulfurization process comprises absorption and removing of sulfur containing compounds from the third stream by an adsorbent.

4. The method of claim 1, wherein in the butane isomerization unit the third stream is contacted with an isomerization catalyst under conditions comprising a temperature of 130° C. to 300° C., a pressure 10 to 40 bar, a WHSV 0.5 $h^{-1}$ to 10 $h^{-1}$ or any combination thereof.

5. The method of claim 4, wherein the isomerization catalyst is a platinum chlorinated alumina ($Pt/Al_2O_3$—Cl) catalyst, a platinum zirconia sulfate catalyst ($Pt/ZrO_2$—$SO_4$) and/or an iso shape selective zeolites.

6. The method of claim 1, wherein a feed stream comprising n-butane is fed to the butane isomerization unit and the fourth stream further comprises n-butane and iso-butane.

7. The method of claim 6, wherein the third stream and the feed stream is fed to the butane isomerization unit as separate feeds or as a combined feed.

8. The method of claim 1, comprising subjecting the fourth stream to the DIB unit.

9. The method of claim 1, wherein the DIB unit comprises a DIB column and the DIB column operation condition to obtain the first stream comprises a temperature of 50 to 60° C., a reboiler range of 90 to 100° C., or an operation gauge pressure of 1 to 5 bar, or any combination thereof.

10. The method of claim 1, wherein the first stream comprises 30 wt. % to 70 wt. % iso-pentane, 15 wt. % to 35 wt. % n-pentane, and 1 wt. % to 15 wt. % neo-pentane.

11. The method of claim 1, wherein during the separation of the first stream in step (a) the separation column operation condition comprises an overhead boiling range temperature of 50° C. to 65° C., a reboiler range of 80° C. to 100° C., or an operation gauge pressure of 3 to 6 bar, or any combination thereof.

12. The method of claim 1, wherein the second stream comprises 70 wt. % to 98 wt. % of iso-pentane, 0 wt. % to 30 wt. % of n-pentane and neo-pentane or less than 5 wt. % of sulfur or any combination thereof.

13. The method of claim 1, wherein the third stream comprises 90 wt. % to 99.5 wt. % n-pentane and 0 wt. % to 10 wt. % neo-pentane.

14. The method of claim 1, wherein the first stream further comprises n-butane, and in step (a) the first stream is separated to obtain the second stream, the third stream and a fifth stream comprising n-butane.

15. The method of claim 1, wherein the iso-pentane of the second stream is used as a blend stock for gasoline and/or blend stock for MTBE.

* * * * *